United States Patent
Hotter et al.

(10) Patent No.: US 9,732,053 B2
(45) Date of Patent: Aug. 15, 2017

(54) 1-[2-(2,4-DIMETHYLPHENYLSULFANYL) PHENYL]PIPERAZINE ACETATE IN CRYSTALLINE FORM

(71) Applicant: LEK PHARMACEUTICALS D.D., Ljubljana (SI)

(72) Inventors: Andreas Hotter, Kundl (AT); Robert Ziegert-Knepper, Kundl (AT); Verena Adamer, Innsbruck (AT); Arthur Pichler, Kundl (AT)

(73) Assignee: LEK PHARMACEUTICALS D.D., Ljubljana (SI)

( * ) Notice: Subject to any disclaimer, the term of this patent is extended or adjusted under 35 U.S.C. 154(b) by 0 days.

(21) Appl. No.: 14/902,326

(22) PCT Filed: Jun. 30, 2014

(86) PCT No.: PCT/EP2014/063823
§ 371 (c)(1),
(2) Date: Dec. 30, 2015

(87) PCT Pub. No.: WO2015/000833
PCT Pub. Date: Jan. 8, 2015

(65) Prior Publication Data
US 2016/0289202 A1  Oct. 6, 2016

(30) Foreign Application Priority Data
Jul. 1, 2013 (EP) .................................. 13174497

(51) Int. Cl.
*C07D 295/096* (2006.01)
*C07C 53/10* (2006.01)

(52) U.S. Cl.
CPC .......... *C07D 295/096* (2013.01); *C07C 53/10* (2013.01)

(58) Field of Classification Search
CPC ............................ C07C 53/10; C07D 295/096
See application file for complete search history.

(56) References Cited

U.S. PATENT DOCUMENTS

2010/0297240 A1* 11/2010 Bang-Andersen . C07D 295/096
424/489

FOREIGN PATENT DOCUMENTS

WO  WO 2007/144005 A1  12/2007
WO  WO 2010/121621 A1  10/2010

OTHER PUBLICATIONS

International Search Report issued in PCT/EP2014/063823, mailed on Aug. 20, 2014.

* cited by examiner

*Primary Examiner* — Michael B Pallay
(74) *Attorney, Agent, or Firm* — Arent Fox LLP

(57) ABSTRACT

The present invention relates to 1-[2-(2,4-dimethylphenylsulfanyl)phenyl]piperazine acetate in crystalline form and to methods for the preparation thereof. In addition the present invention relates to solid pharmaceutical compositions for oral administration comprising an effective amount of the crystalline 1-[2-(2,4-dimethylphenylsulfanyl)phenyl]piperazine acetate. Moreover, the present invention relates to the use of crystalline 1-[2-(2,4-dimethylphenylsulfanyl)phenyl] piperazine acetate for the preparation of pharmaceutical compositions.

14 Claims, 8 Drawing Sheets

1-[2-(2,4-DIMETHYLPHENYLSULFANYL) PHENYL]PIPERAZINE ACETATE IN CRYSTALLINE FORM

CROSS-REFERENCE TO RELATED APPLICATIONS

This application is a National Stage entry of International Application No. PCT/EP2014/063823, filed Jun. 30, 2014, which claims priority to European Patent Application No. 13174497.1, filed Jul. 1, 2013. The disclosures of the prior applications are hereby incorporated in their entirety by reference.

FIELD OF THE INVENTION

The present invention relates to 1-[2-(2,4-dimethylphenylsulfanyl)phenyl]piperazine acetate in crystalline form and to methods for the preparation thereof. In addition the present invention relates to solid pharmaceutical compositions for oral administration comprising an effective amount of crystalline 1-[2-(2,4-dimethylphenylsulfanyl)phenyl]piperazine acetate. Moreover, the present invention relates to the use of crystalline 1-[2-(2,4-dimethylphenylsulfanyl)phenyl]piperazine acetate for the preparation of pharmaceutical compositions.

BACKGROUND OF THE INVENTION

1-[2-(2,4-Dimethylphenylsulfanyl)phenyl]piperazine, also known as vortioxetine, is a multimodal serotonergic compound intended to be used in the treatment of major depressive disorder and generalized anxiety disorder. The compound shows antagonistic properties at 5-HT$_{3A}$ and 5-HT$_7$ receptors, partial agonistic properties at 5-HT$_{1B}$ receptors, agonistic properties at 5-HT$_{1A}$ receptors and potent serotonin reuptake inhibition via inhibition of the serotonin transporter (SERT). 1-[2-(2,4-Dimethylphenylsulfanyl)phenyl]piperazine is represented by the following general formula (I):

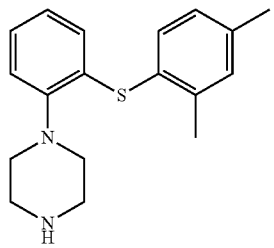

(I)

Vortioxetine free base is disclosed in WO 2003/029232 A1.

WO 2007/144005 A1 discloses crystalline vortioxetine free base, a variety of crystalline polymorphs and pseudo-polymorphs of vortioxetine hydrobromide, including a hemihydrate and an ethyl acetate solvate thereof, crystalline vortioxetine hydrochloride and a monohydrate thereof, and crystalline forms of vortioxetine mesylate, hydrogenfumarate, hydrogenmaleate, mesohydrogentartrate, L-(+)-hydrogentartrate, D-(−)-hydrogentartrate, hydrogen sulphate, dihydrogenphosphate and nitrate.

WO 2010/094285 A1 discloses an isopropanol solvate of vortioxetine hydrobromide as well as a process for the purification of vortioxetine and pharmaceutically acceptable salts thereof.

WO 2010/121621 A1 discloses crystalline forms of vortioxetine L-lactate and vortioxetine DL-lactate.

However, there still remains a need for alternative solid state forms of vortioxetine with improved physicochemical properties such as e.g. improved solubility and bioavailability, low hygroscopicity, high chemical and physical stability, convenient toxicity profile, etc.

The bioavailability of a compound intended to be administered orally is dependent on the compound's solubility as well as the compound's permeability according to the biopharmaceutical classification system (BCS). Therefore a solid state form of vortioxetine having high aqueous solubility, and which is consequently highly orally bioavailable, is desirable.

In addition, an active pharmaceutical ingredient of a solid pharmaceutical formulation preferably shows low hygroscopicity in order to ensure chemical and physical quality during storage of the active substance itself and during the shelf-life of the finished dosage form containing the active substance without the need for special and expensive packaging. Hence, a solid state form of vortioxetine showing low hygroscopicity and consequently being physically and chemically stable when exposed to increased relative humidity is preferable for the preparation of a solid pharmaceutical composition.

Most preferable is a solid state form of vortioxetine combining both high aqueous solubility and low hygroscopicity suitable for the preparation of a solid pharmaceutical composition for oral administration.

SUMMARY OF THE INVENTION

The present invention provides vortioxetine acetate in crystalline form which is surprisingly freely soluble in water and, in certain embodiments, displays an attractive combination of high solubility and low hygroscopicity compared to the known solid state forms of vortioxetine and is thus particularly suitable for the preparation of solid pharmaceutical compositions for oral administration.

In addition, the superior solubility of crystalline vortioxetine acetate makes it the most preferred crystalline salt of vortioxetine for preparing a liquid pharmaceutical composition.

Hence, in a first aspect of the invention, there is provided vortioxetine acetate in crystalline form.

In one embodiment, the present invention relates to a novel polymorph of vortioxetine acetate, referred to hereinafter as vortioxetine acetate form III.

Polymorph III of vortioxetine acetate can be characterized by exhibiting monoclinic unit cells having space group C2/c. Preferably these monoclinic unit cells are characterized by the following parameters as determined by X-ray structural analysis:
a=34.18+/−0.5 Angstrom
b=10.72+/−0.2 Angstrom
c=21.01+/−0.3 Angstrom
α=90.0°
β=97.9°+/−0.5°
γ=90°
Z=16

In addition polymorph III of vortioxetine acetate can be characterized by an X-ray powder diffractogram comprising characteristic peaks at 2-theta angles of 9.7±0.2°, 11.3±0.2°, 13.5±0.2°, 15.6±0.2° and 16.9±0.2° when measured using Cu-Kα radiation.

In one embodiment, the present invention relates to a novel crystalline form of vortioxetine acetate, referred to hereinafter as vortioxetine acetate form I. Crystalline form I of vortioxetine acetate can be characterized by an X-ray powder diffractogram comprising characteristic peaks at 2-theta angles of 6.6±0.2°, 7.2±0.2°, 13.1±0.2°, 14.0±0.2° and 15.7±0.2° when measured using Cu-Kα radiation.

In a second aspect, the present invention relates to a process for preparing crystalline vortioxetine acetate comprising the steps of:
(a) dissolving vortioxetine acetate in a solvent upon heating;
(b) optionally filtering the obtained solution; and
(c) cooling the solution in order to initiate crystallization.

In a third aspect, the present invention relates to pharmaceutical compositions comprising an effective amount of crystalline vortioxetine acetate and a pharmaceutically acceptable carrier.

In a fourth aspect, the present invention relates to the use of crystalline vortioxetine acetate for the preparation of pharmaceutical compositions.

In a fifth aspect, the present invention relates to crystalline vortioxetine acetate for use as a medicament, in particular for use in the treatment of mood disorders; major depressive disorder; general anxiety disorder; post-traumatic stress disorder; depression associated with cognitive impairment, Alzheimer's disease or anxiety; depression with residual symptoms; chronic pain; or eating disorders.

In the context of the present invention, the following abbreviations have the indicated meaning, unless explicitly stated otherwise:
XRPD: X-ray powder diffraction/diffractogram
FTIR: Fourier transform infrared spectroscopy/spectrum
DSC: Differential scanning calorimetry
TGA: Thermogravimetric analysis
RT: room temperature
RH or r.h.: relative humidity

DETAILED DESCRIPTION OF THE INVENTION

As used herein the term "room temperature" indicates that the applied temperature is not critical and that no exact temperature value has to be kept. Usually, "room temperature" is understood to mean temperatures of about 15° C. to about 25° C. [see e.g. European Pharmacopoeia 7.6, 1.2 (2013)].

The term "solid state forms of vortioxetine" as used herein refers to amorphous and crystalline forms (comprising polymorphs, hydrates and solvates) of vortioxetine free base, vortioxetine acid addition salts and vortioxetine co-crystals.

The term "crystalline vortioxetine acetate" as used herein includes all polymorphic forms of crystalline vortioxetine acetate. Reference to crystalline vortioxetine acetate is to be interpreted as equivalent to a reference to vortioxetine acetate form I and/or vortioxetine acetate form III.

In a first aspect of the invention, the present invention relates to crystalline vortioxetine acetate. In one embodiment, there is provided a novel polymorph of 1-[2-(2,4-dimethylphenylsulfanyl)phenyl]piperazine acetate (hereinafter also referred to as vortioxetine acetate form III). 1-[2-(2,4-dimethylphenylsulfanyl)phenyl]piperazine acetate is represented by the following general formula (II):

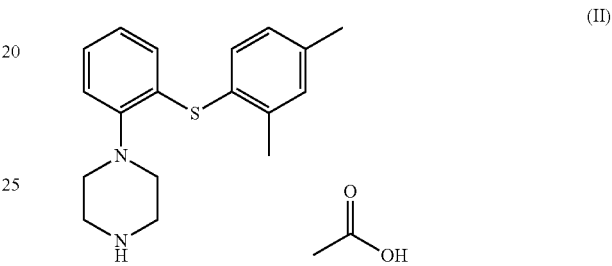

(II)

Form III of vortioxetine acetate can be characterized by exhibiting monoclinic unit cells having space group C2/c.

Preferably these monoclinic unit cells are characterized by the following parameters as determined by X-ray structural analysis:
a=34.18+/−0.5 Angstrom
b=10.72+/−0.2 Angstrom
c=21.01+/−0.3 Angstrom
α=90.0°
β=97.9°+/−0.5°
γ=90°
Z=16

Figure 1:
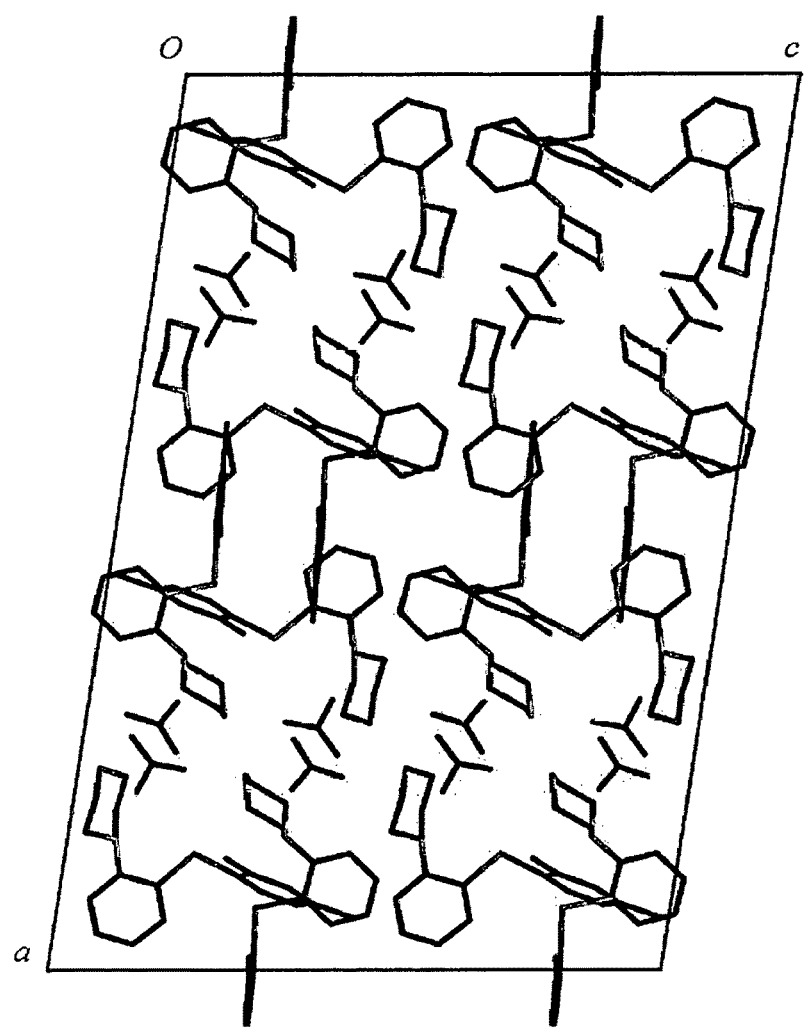
FIG. 1: Unit cell of vortioxetine acetate form III

According to single X-ray structure analysis the molar vortioxetine/acetic acid ratio is 1:1 for form III of the present invention (see also unit cell in FIG. 1).

In addition, form III of vortioxetine acetate can be characterized by showing an X-ray powder diffractogram comprising characteristic peaks at 2-theta angles of 9.7±0.2°, 11.3±0.2°, 13.5±0.2°, 15.6±0.2° and 16.9±0.2° when measured using Cu-Kα radiation.

In addition, form III of vortioxetine acetate can be characterized by showing an X-ray powder diffractogram comprising characteristic peaks at 2-theta angles of 8.4±0.2°, 9.7±0.2°, 11.3±0.2°, 11.8±0.2°, 13.5±0.2°, 15.6±0.2° and 16.9±0.2° when measured using Cu-Kα radiation.

In addition, form III of vortioxetine acetate can be characterized by showing an X-ray powder diffractogram comprising characteristic peaks at 2-theta angles of 8.4±0.2, 9.7±0.2°, 10.5±0.2°, 11.3±0.2°, 11.8±0.2°, 12.5±0.2°, 13.5±0.2°, 15.6±0.2°, 16.9±0.2° and 18.5±0.2° when measured using Cu-Kα radiation.

Figure 2:
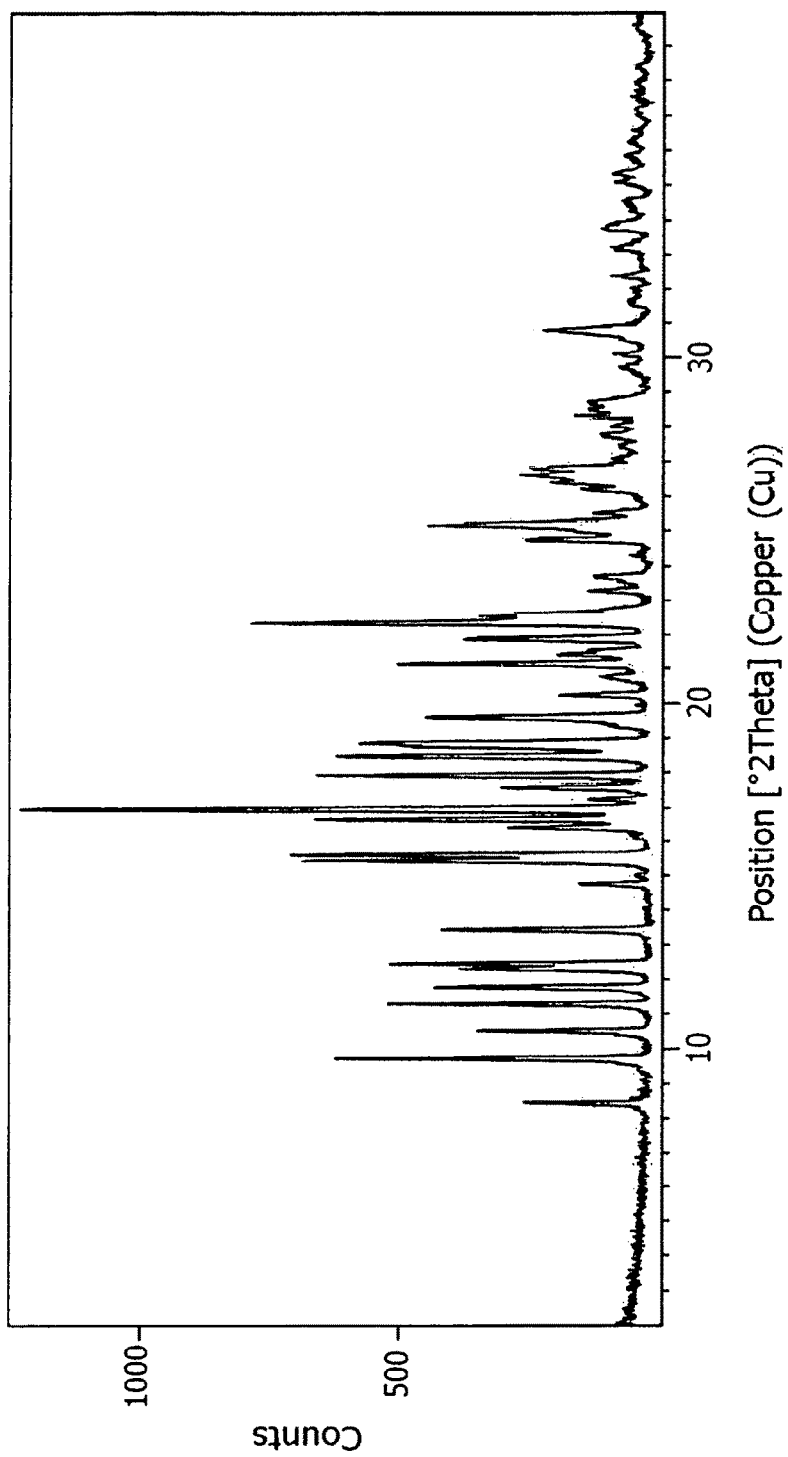
FIG. 2: X-ray powder diffractogram of vortioxetine acetate form III

The X-ray powder diffractogram of form III of vortioxetine acetate comprises additional characteristic peaks at 2-theta angles of 12.3±0.2°, 14.8±0.2°, 15.5±0.2°, 16.4±0.2°, 16.6±0.2°, 17.2±0.2°, 17.6±0.2°, 17.9±0.2°, 18.9±0.2°, 19.6±0.2°, 20.2±0.2°, 21.1±0.2°, 21.4±0.2°, 21.9±0.2° 22.3±0.2°, 22.6±0.2°, 24.7±0.2°, 25.1±0.2°, 26.2±0.2°, 26.4±0.2°, 26.6±0.2°, 26.8±0.2°, 28.3±0.2° and 30.8±0.2°. A representative diffractogram is displayed in FIG. 2. In one embodiment of the invention, there is therefore provided crystalline vortioxetine acetate having an X-ray powder diffraction pattern substantially the same as the X-ray powder diffraction pattern shown in FIG. 2 when measured using Cu-Kα radiation.

Figure 3:
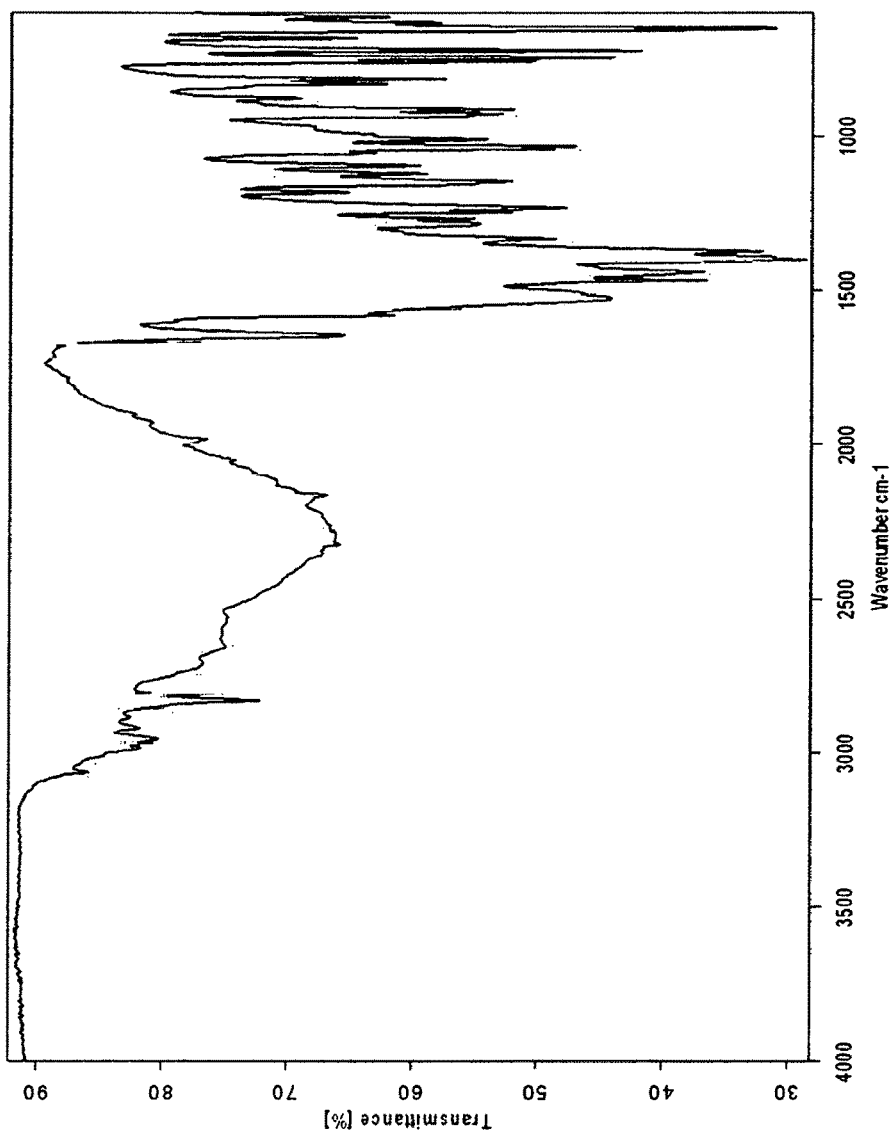
FIG. 3: Fourier transform infrared spectrum of vortioxetine acetate form III

In addition, form III of vortioxetine acetate can be characterized by showing an FTIR-spectrum comprising characteristic peaks at wavenumbers of 2828±2 cm$^{-1}$, 1645±2 cm$^{-1}$, 1527±2 cm$^{-1}$, 1402±2 cm$^{-1}$ and 653±2 cm$^{-1}$. The FTIR-spectrum of form III of vortioxetine acetate comprises additional characteristic peaks at wavenumbers of 3062±2 cm$^{-1}$, 2955±2 cm$^{-1}$, 1581±2 cm$^{-1}$, 1469±2 cm$^{-1}$, 1441±2 cm$^{-1}$, 1374±2 cm$^{-1}$, 1333±2 cm$^{-1}$, 1287±2 cm$^{-1}$, 1268±2 cm$^{-1}$, 1247±2 cm$^{-1}$, 1234±2 cm$^{-1}$, 1184±2 cm$^{-1}$, 1149±2 cm$^{-1}$, 1124±2 cm$^{-1}$, 1095±2 cm$^{-1}$, 1041±2 cm$^{-1}$, 1033±2 cm$^{-1}$, 1010±2 cm$^{-1}$, 928±2 cm$^{-1}$, 914±2 cm$^{-1}$, 877±2 cm$^{-1}$, 829±2 cm$^{-1}$, 814±2 cm$^{-1}$, 758±2 cm$^{-1}$, 745±2 cm$^{-1}$, 724±2 cm$^{-1}$ and 684±2 cm$^{-1}$. A representative FTIR spectrum is displayed in FIG. 3. In one embodiment of the invention, there is therefore provided crystalline vortioxetine acetate having an FTIR spectrum substantially the same as the FTIR spectrum shown in FIG. 3.

Figure 4:
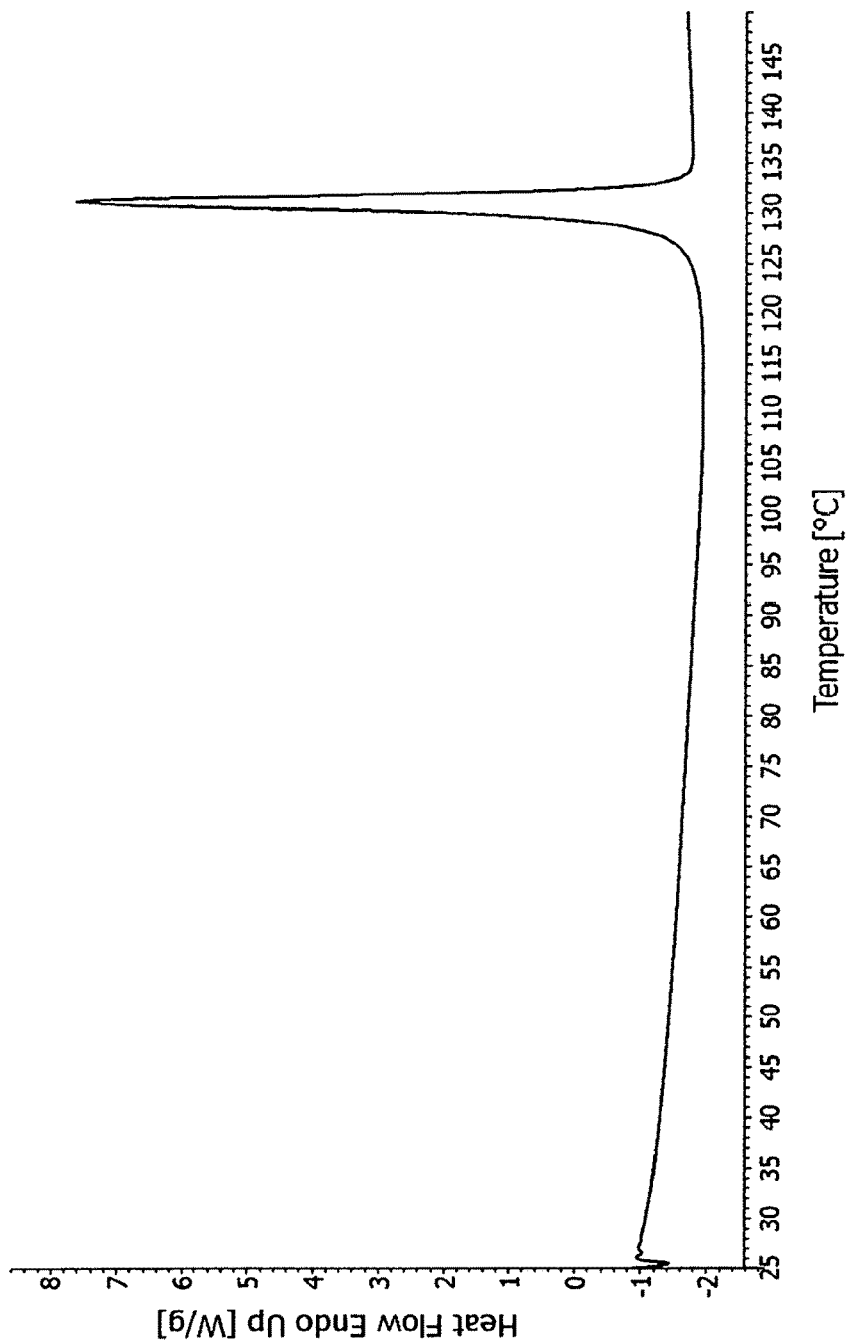
FIG. 4: Differential Scanning calorimetry thermogram of vortioxetine acetate form III

Moreover form III of vortioxetine acetate can be characterized by a differential scanning calorimetric curve showing a single melting endotherm with an onset of about 129° C. and a maximum at about 131° C. A representative DSC thermogram is displayed in FIG. 4. In one embodiment of the invention, there is therefore provided crystalline vortioxetine acetate having a differential scanning calorimetric curve substantially the same as the differential scanning calorimetric curve shown in FIG. 4.

Figure 5:
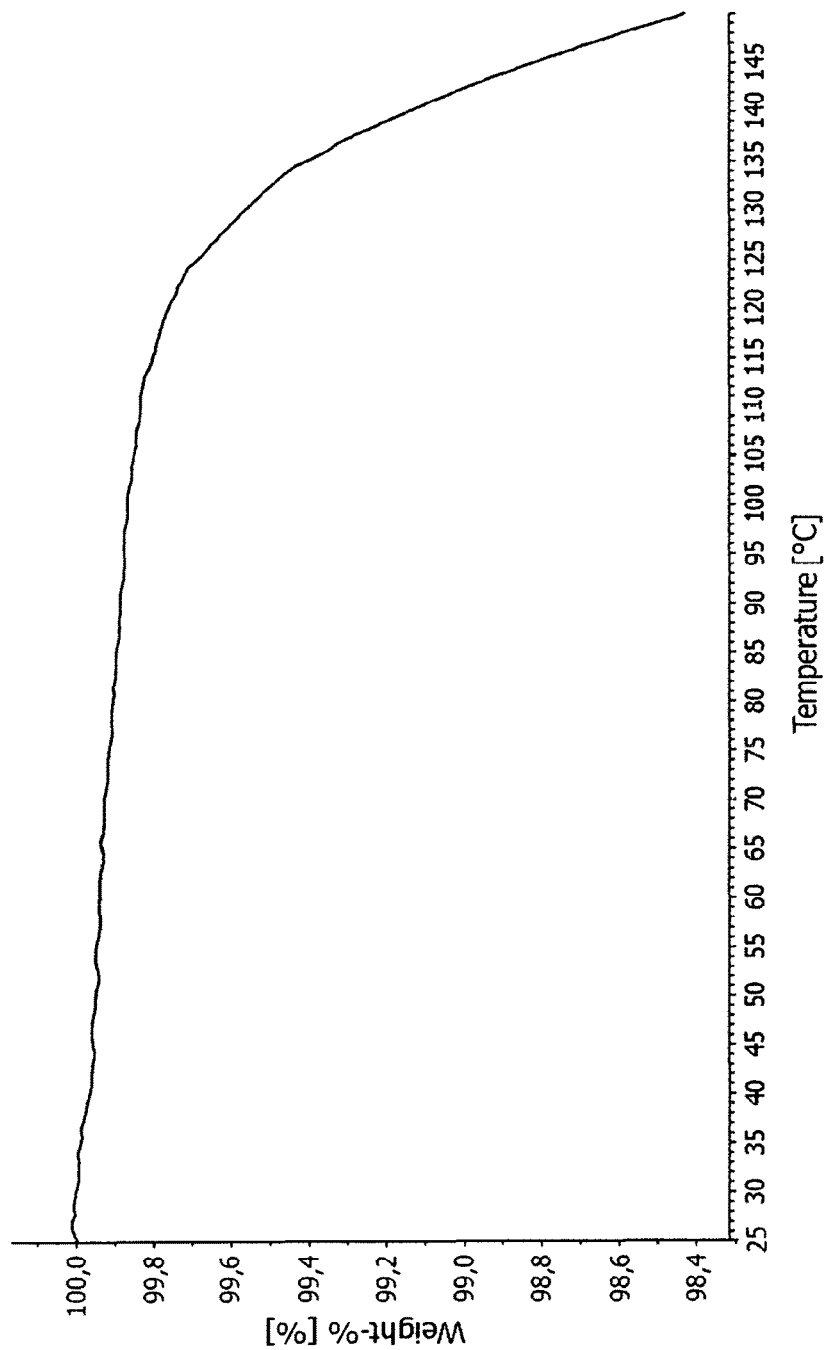
FIG. 5: Thermogravimetric analyses curve of vortioxetine acetate form III

Furthermore form III of vortioxetine acetate can be characterized as being a non-solvated form containing less than about 0.5% of an organic solvent as determined by thermogravimetric analysis. The representative TGA curve displayed in FIG. 5 shows a mass loss of about 0.4% until melting at about 130° C.

Figure 6:
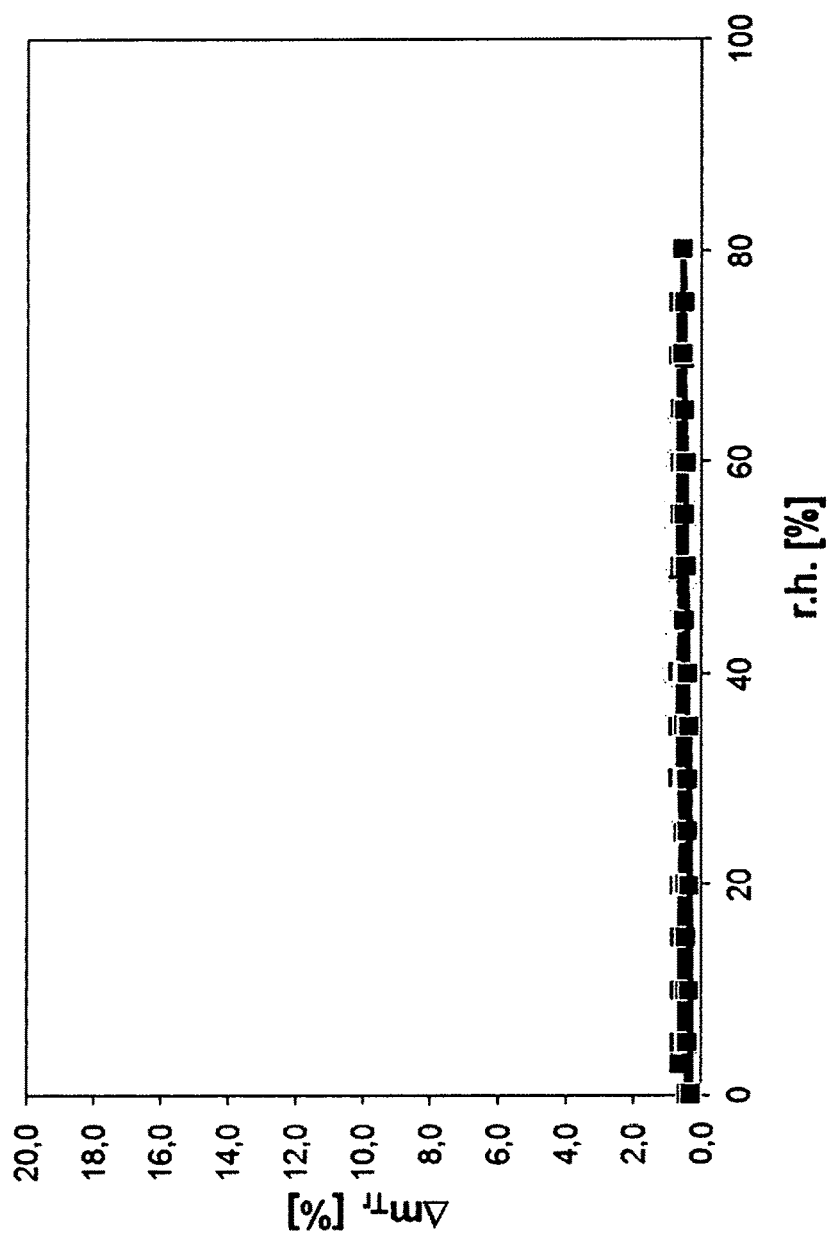
FIG. 6: Gravimetric moisture sorption/desorption cycle of vortioxetine acetate form III

Finally form III of vortioxetine acetate can be characterized as being an anhydrous form. E.g. form III contains less than about 0.7% water up to a relative humidity of about 80%. A representative gravimetric moisture sorption/desorption cycle is displayed in FIG. 6.

In a second aspect the present invention relates to a process for the preparation of crystalline vortioxetine acetate comprising the steps of:
  (a) dissolving vortioxetine acetate in a solvent upon heating,
  (b) optionally filtering the obtained solution and
  (c) cooling the solution in order to initiate crystallization.

Any solid state form of vortioxetine acetate can be applied in the process as starting material, for example crystalline vortioxetine acetate, amorphous vortioxetine acetate or mixtures thereof. A suitable crystalline form is, for example, form I of the present invention, which can be prepared by reacting vortioxetine base with acetic acid in the presence of a suitable solvent such as n-heptane or tert-butylmethyl ether, for example according to example 7 of the present invention. The vortioxetine base used for form I production can be prepared according to example 1e of WO 2003/029232 A1.

In a first step, vortioxetine acetate starting material is dissolved in a suitable solvent. Suitable solvents are, for example, tert-butylmethyl ether, diisopropyl ether, n-butyl acetate, isobutyl acetate, toluene, acetone or mixtures thereof. Depending on the vortioxetine acetate concentration, its solid state form and the solvent used in the process, the dissolution temperature may range from 40° C. to reflux temperature. Typically reflux temperature is applied to completely dissolve the starting material. The initial vortioxetine acetate concentration typically ranges from 5 to 200 g/L, more preferably from 5 to 150 g/L and most preferably from 5 to 125 g/L. After the vortioxetine acetate starting material has dissolved, an optional filtration step may be applied, whereupon the solution may be treated with charcoal prior to filtration. Thereafter the solution is cooled to 0-30° C., preferably to about room temperature, which typically initiates the crystallization of form III of vortioxetine acetate. The cooling rate is not critical and may range from 0.1° C./min to 10.0° C./min, preferably from 0.3° C./min to 5.0° C./min and most preferably from 0.5° C./min to 2.0° C./min.

Sometimes it may be necessary to further concentrate the solution in order to initiate crystallization. This can be achieved by evaporating the solvent naturally or under reduced pressure and/or increased temperature.

Finally, the crystals so obtained are collected by any conventional method such as filtration or centrifugation, preferably by filtration.

The particle size of vortioxetine acetate form III obtained according to the process of the present invention typically ranges from 10 to 1,000 μm as determined by optical light microscopy. However, the particle size can be decreased by any conventional method such as milling or grinding. In addition, the particle size can be homogenized by applying an additional sieving step. Preferably milling and sieving are performed in such a manner that vortioxetine acetate form III having a particle size ranging from 0.1 to 50 μm, preferably from 0.1 to 25 μm and most preferably from 0.1 to 15 μm is obtained.

The bioavailability of a compound intended to be administered orally is dependent on the compound's solubility as well as the compound's permeability according to the biopharmaceutical classification system (BCS). Therefore, a solid state form of vortioxetine having high aqueous solubility, which is consequently highly orally bioavailable, is desirable.

WO 2007/144005 A1 and WO 2010/121621 A1 provide aqueous solubility data for different vortioxetine salts, the mesylate salt of vortioxetine (>45 mg base/mL) showing the highest solubility. Table 1 summarizes the solubility data of the solid state forms provided by the prior art.

TABLE 1

Aqueous solubilities at room temperature

| Literature source | Vortioxetine salt | Aqueous solubility [mg base/mL] |
| --- | --- | --- |
| WO 2007/144005 A1 | free base | 0.1 |
| WO 2007/144005 A1 | HBr form α | 2 |
| WO 2007/144005 A1 | HBr form β | 1.2 |
| WO 2007/144005 A1 | HCl | 3 |
| WO 2007/144005 A1 | HCl MH | 2 |
| WO 2007/144005 A1 | mesylate | >45 |
| WO 2007/144005 A1 | fumarate | 0.4 |
| WO 2007/144005 A1 | maleate | ≈1 |
| WO 2007/144005 A1 | meso-tartrate | ≈0.7 |
| WO 2007/144005 A1 | L-(+)-tartrate | ≈0.4 |
| WO 2007/144005 A1 | D-(−)-tartrate | ≈0.4 |
| WO 2007/144005 A1 | sulphate | ≈0.1 |
| WO 2007/144005 A1 | phosphate | ≈1 |
| WO 2007/144005 A1 | nitrate | ≈0.8 |
| WO 2010/121621 A1 | L-lactate form MH2 | 26 |
| WO 2010/121621 A1 | DL-lactate form β | 8 |

Surprisingly, form III of vortioxetine acetate of the present invention shows a significantly increased aqueous solubility compared to the prior art solid state forms of vortioxetine. The aqueous solubility at room temperature of vortioxetine acetate form III of the present invention was found to be 278 mg base/mL, see Example 9. As vortioxetine acetate form III clearly shows the highest aqueous solubility, according to the BCS it represents the best orally bioavailable solid state form, making this particular solid state form especially suitable for the preparation of an orally administered medicament.

Although for many pharmaceutical compounds oral administration in the form of a tablet or capsule is preferred, some patients, for example elderly and pediatric patients, may have difficulties in swallowing such formulations. Therefore, liquid formulations such as oral solutions may offer a suitable alternative, avoiding the need of swallowing tablets or capsules. An oral solution further provides the possibility of a more flexible dosing regimen. In order to limit the volume of an oral solution it is necessary to have a high concentration of the active ingredient in the solution, which again requires a high solubility of the active ingredient. Hence the superior solubility of form III of vortioxetine acetate of the present invention makes this particular solid state form especially suitable for the preparation of liquid pharmaceutical formulations such as oral solutions.

In addition, an active pharmaceutical ingredient intended for use as a solid pharmaceutical composition preferably shows low hygroscopicity in order to ensure chemical and physical quality during storage of the active substance itself and during the shelf-life of the solid finished dosage form containing the active substance, without the need for special and expensive packaging.

The most soluble solid state form of vortioxetine described by the prior art, namely vortioxetine mesylate disclosed in WO 2007/144005 A1, significantly takes up water at increased relative humidity and transforms into a hydrated form as described by example 6b of WO 2007/144005 A1. Hence, although showing relatively good solubility, the mesylate salt of WO 2007/144005 A1 is not preferred for the preparation of a solid pharmaceutical formulation due to its low physical stability at increased relative humidity.

Figure 8:
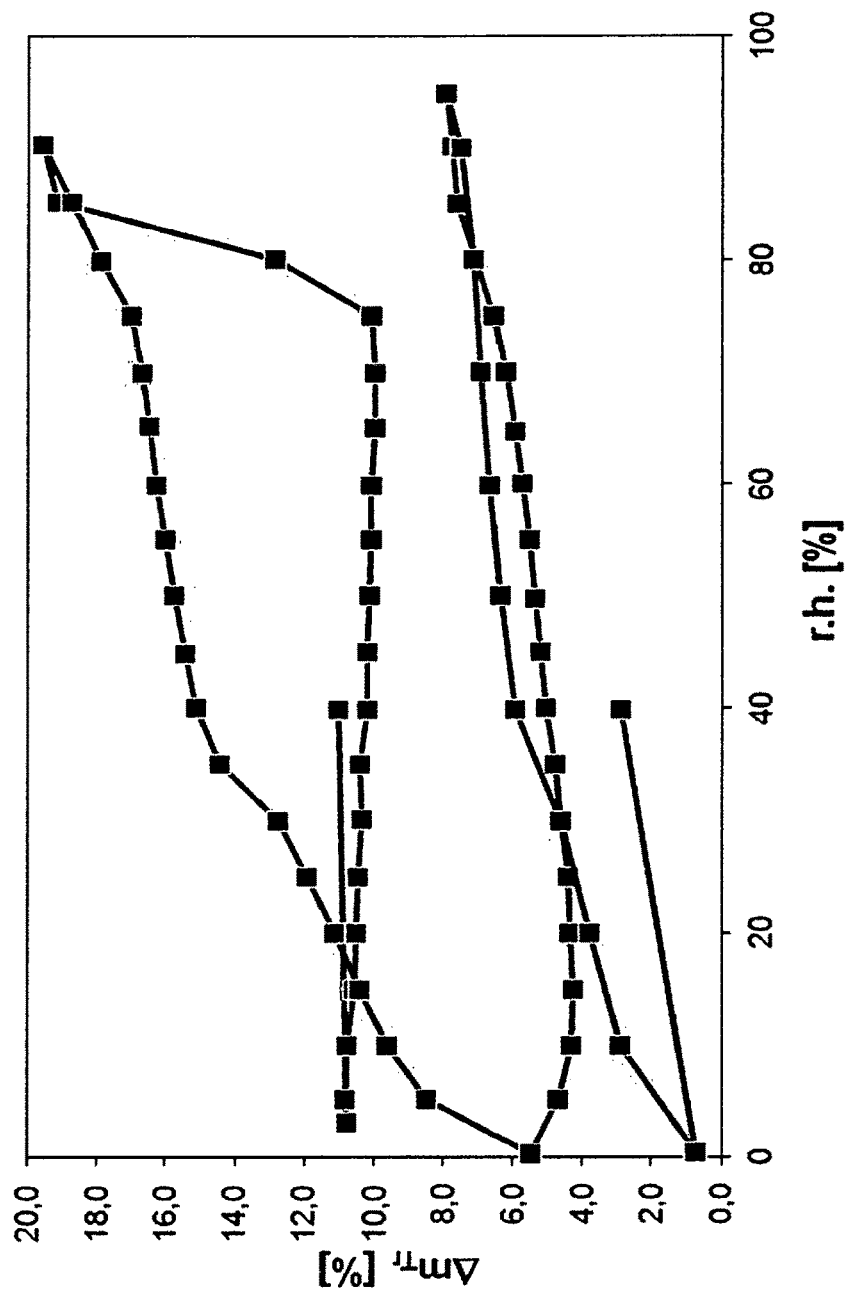
FIG. 8: Gravimetric moisture sorption/desorption cycle of vortioxetine acetate form I

The gravimetric moisture sorption desorption curve of form I in FIG. 8 shows a mass increase of 2% between 0 and 80% RH. During the gravimetric moisture sorption measurement partial decomposition of the acetate salt to the free base of vortioxetine occurred, as confirmed by XRPD analysis at the end of the sorption desorption cycle. Hence, form I is also not preferred for the preparation of solid pharmaceutical formulations due to its low chemical stability at increased relative humidity.

In contrast, vortioxetine acetate form III of the present invention showed no structural changes after stressing it at RT/97% RH or 40° C./75% RH for 4 weeks, which was confirmed by XRPD (see also examples 10-11 of the present invention). The gravimetric moisture sorption desorption curve in FIG. 6 of the present invention shows that form III of vortioxetine acetate is only slightly hygroscopic according to the specifications of the European Pharmacopoeia. It contains about 0.3% water at a relative humidity of about 0% and about 0.7% water at a relative humidity of about 80%. Consequently vortioxetine acetate form III of the present invention is especially suitable for the preparation of a solid pharmaceutical composition.

TABLE 2

Water absorption from 0-80% RH

| Vortioxetine salt | Δm (0-80% RH) | Structural changes |
|---|---|---|
| mesylate of WO 2007/144005 A1 | +8% | hydrate formation at 80% disclosed in WO 2007/144005 A1 |
| acetate form I of present invention | +2% | partial decomposition to free base during sorption desorption cycle |
| acetate form III of present invention | +0.4% | no changes from 0-97% RH |

Slurry experiments were performed to determine the order of the thermodynamic stability of the solid state forms at room temperature (see also Examples 12-13 of the present invention). Form I of vortioxetine acetate undergoes a transition to form III when slurried in n-heptane thus demonstrating that it is a metastable form. However, form III does not undergo any transformation when stirred for 4 weeks in n-heptane and can thus be considered the more thermodynamically stable form at room temperature.

In summary, vortioxetine acetate form III of the present invention shows the most attractive combination of high solubility, low hygroscopicity and sufficient physical and chemical stability and is therefore the most suitable solid state form of vortioxetine for the preparation of solid pharmaceutical formulations for oral administration such as tablets or capsules. Due to its superior solubility, vortioxetine acetate form III is a favored solid state form of vortioxetine for preparing liquid pharmaceutical compositions such as oral solutions.

Thus polymorph III of vortioxetine acetate is the most favored form to be used in oral pharmaceutical compositions and may advantageously be employed in various pharmaceutical formulations for use in the treatment of mood disorders such as depression and anxiety and also for the treatment of cognitive impairment and pain.

Therefore, in a third aspect, the present invention relates to pharmaceutical compositions comprising an effective amount of vortioxetine acetate in crystalline form, in particular vortioxetine acetate form III, and a pharmaceutically acceptable carrier.

Preferably the present invention relates to solid pharmaceutical compositions, wherein more than 95% of vortioxetine acetate is stably present as vortioxetine acetate form III, more preferably wherein vortioxetine acetate form III is the only detectable crystalline form of vortioxetine acetate. The absence of other crystalline forms of vortioxetine acetate, such as form I, can be tested by comparing an XRPD taken of any crystalline vortioxetine acetate with the XRPD of form III as obtained, for example from Example 1 and shown in FIG. 2, which for this comparison can be taken as an XRPD of 100% form III.

"Stably present" as defined herein means that even after storage of the pharmaceutical composition for 180 days, and preferably even after storage for 3 years, the crystalline form of vortioxetine acetate designated as vortioxetine acetate form III initially comprised in the pharmaceutical composition is still present as vortioxetine acetate form III after storage for the indicated period.

The solid pharmaceutical compositions of the present invention comprising crystalline vortioxetine acetate may further comprise one or more pharmaceutically acceptable excipients. Such excipients are preferably selected from the group consisting of diluents, glidants, lubricants, wetting agents, binders and disintegrants. Other excipients known in the field of pharmaceutical compositions may also be used. Furthermore, the pharmaceutical composition may comprise a combination of two or more excipients selected from members of the above mentioned group.

Suitable wetting agents for solid pharmaceutical compositions comprising crystalline vortioxetine acetate include, for example, sodium lauryl sulphate, sodium dioctyl sulfosuccinate, sodium starch glyocolate or wetting agents belonging to the group of polyethylene glycol sorbitan fatty acid esters, such as Tween, for example, Tween 20, 60 and 80.

Suitable binders which can be used for solid pharmaceutical compositions comprising crystalline vortioxetine acetate include, for example, alkylcelluloses such as methylcellulose, hydroxyalkylcelluloses such as hydroxymethylcellulose, hydroxyethylcellulose, hydroxypropylcellulose and hydroxybutylcellulose, hydroxyalkylalkylcelluloses such as hydroxyethylmethylcellulose and hydroxypropylmethylcellulose, carboxyalkylcelluoses such as carboxymethylcellulose, alkali metal salts of carboxyalkylcelluloses such as sodium carboxymethylcellulose, carboxyalkylalkylcelluloses such as carboxymethylethylcellulose, carboxyalkylcellulose esters, starches such as starch 1551, pectins such as sodium carboxymethylamylopectin, chitin derivatives such as chitosan, heparin and heparinoids, polysaccharides such as alginic acid, alkali metal and ammonium salts thereof, carrageenans, galactomannans, tragacanth, agar-agar, gum arabic, guar gum and xanthan gum, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, polyalkylene oxides such as polyethylene oxide and polypropylene oxide and copolymers of ethylene oxide and propylene oxide, for example poloxamers and poloxamines, copovidone.

Suitable diluents which can be used for solid pharmaceutical compositions comprising crystalline vortioxetine acetate include, for example, calcium carbonate, dibasic calcium phosphate, dibasic calcium phosphate dihydrate, tribasic calcium phosphate, calcium sulphate, microcrystalline cellulose including silicified microcrystalline cellulose, powdered cellulose, dextrates, dextrin, dextrose excipient, fructose, kaolin, lactitol, lactose anhydrous, lactose monohydrate, mannitol, sorbitol, starch, modified starch, sodium chloride, sucrose, compressible sugar, confectioner's sugar, a spray-dried mixture of lactose monohydrate and microcrystalline cellulose (75:25), commercially available as Microcelac®, a co-processed spray-dried mixture of microcrystalline cellulose and colloidal silicon dioxide (98:2), commercially available as Prosolv®.

Suitable glidants which can be used for solid pharmaceutical compositions comprising crystalline vortioxetine acetate include, for example, talc, colloidal silicon dioxide, starch and magnesium stearate.

Suitable disintegrants which can be used for solid pharmaceutical compositions comprising crystalline vortioxetine acetate include, for example, starch, ion exchange resins, such as Amberlite, cross-linked polyvinylpyrrolidone, modified cellulose gum, such as croscarmellose sodium, sodium starch glycolate, sodium carboxymethylcellulose, sodium dodecyl sulphate, modified corn starch, microcrystalline cellulose, magnesium aluminium silicate, alginic acid, alginate and powdered cellulose.

Suitable lubricants which can be used for solid pharmaceutical compositions comprising crystalline vortioxetine acetate include, for example, magnesium stearate, calcium stearate, stearic acid, talc, polyethylene glycol, sodium lauryl sulphate and magnesium lauryl sulphate.

In addition, solid pharmaceutical compositions comprising crystalline vortioxetine acetate may comprise other optional excipients such as flavours, sweeteners and colouring agents.

Orally administered vortioxetine is known to cause irritations of the gastric mucosa leading to gastrointestinal disturbances such as nausea and vomiting (Lundbeck, Corporate Release No. 501, 18 May 2013, Valby, Denmark). Hence solid pharmaceutical compositions comprising crystalline vortioxetine acetate are preferably enteric coated pharmaceutical compositions such as an enteric coated tablets or enteric coated capsules.

Enteric film coatings which can also be used for solid pharmaceutical compositions comprising crystalline vortioxetine acetate preferably comprise a film-forming polymer, optionally a plasticizer, optionally an anti-adhesion agent, optionally a colouring agent, optionally an antifoaming agent, optionally an emulsifier, optionally a stabilizer and/or optionally a wetting agent.

Suitable enteric film-forming polymers which can be used for solid pharmaceutical compositions comprising crystalline vortioxetine acetate comprise, for example, polymethacrylates such as methacrylic acid ethacrylate poly ($MA_1$-$EA_1$) and methacrylic acid methyl methacrylate poly ($MA_1$-$MMA_1$ or $MA_1$-$MMA_2$) cellulose derivatives such as ethylcellulose, carboxymethylcellulose, methylcellulose phtalate, cellulose acetate phtalate, cellulose acetate trimellitate, cellulose acetate succinate, hydroxypropyl cellulose phtalate, hydroxypropylmethyl cellulose phtalate, hydroxypropylethyl cellulose phtalat and hydroxypropylmethyl cellulose acetate succinate, polyvinyl derivatives such as polyvinyl acetate phtalate or polyvinylpyrrolidone acetate phtalate, other copolymers such as half esters of the copolymerisate of styrene and maleic acid, half esters of the copolymerisate of vinyl ether and maleic acid and copolymerisate of vinyl acetate and crotonic acid, shellac or mixtures thereof. Suitable commercially available ready to use enteric film coatings which can be applied for the preparation of pharmaceutical compositions of the present invention include, for example, Aquateric, Aquacoat Surelease, Aquoat, LF, Aquoat MF, Aquoat HF, CAP, CAT, Coateric, Duodcell, Eudragit L30D, Eudragit L, Eudragit S, Eudragit NE30D, Eudragit RL or Eudragit RS, HP 50, HP 55, HP 55 S, HP 50 F, HP 55 F S, HPMCP 55, HPMCP 55, Opadry (Aqueous) Enteric.

Suitable plasticizers which can be used for solid pharmaceutical compositions comprising crystalline vortioxetine acetate include, for example, alkyl esters of citric, tartaric and sebacic acids such as diethyl sebacate, triethyl citrate, tributyl citrate, acetyltriethyl citrate, acetyltributyl citrate and dibutyl tartrate, esters of phtalic acid such as dimethyl phtalate, diethyl phtalate, dibutyl phtalate, dioctyl phtalate, ethylphtaloyl ethyl glycolate and butylphtaloyl ethyl glycolate, glycerol esters such as castor oil, sesame oil, acetylated fatty acid glycerides, glycerol diacetate and glycerol triacetate (triacetin), higher alcohols such as glycerol and 1,2-propylene glycol, polyethers such as polyethyleneglycol 400 to 6000 and polyoxyethylene-polyoxypropylene block copolymers, surfactants such as PEG-400 stearate, PEG sorbitane monooleate and sorbitane monooleate or mixtures thereof.

Suitable anti-adhesion agents which can be used for solid pharmaceutical compositions comprising crystalline vortioxetine acetate include, for example, talc, magnesium stearate, micronized amorphous silicic acid (Syloid®), fumed silica (Aerosil®), kaolin or mixtures thereof.

Suitable colouring agents which can be used for solid pharmaceutical compositions comprising crystalline vortioxetine acetate include, for example, titanium dioxide and pigments such as foodstuff colouring lakes and iron oxide pigments.

Suitable antifoaming agents which can be used for solid pharmaceutical compositions comprising crystalline vortioxetine acetate include, for example, silicon emulsions and sorbitan sesquioleate.

A suitable suspension stabilizer which can be used for solid pharmaceutical compositions comprising crystalline vortioxetine acetate is polyvinylpyrrolidone.

Suitable emulsifiers and wetting agents which can be used for solid pharmaceutical compositions comprising crystalline vortioxetine acetate include, for example, polyethylene glycol sorbitan fatty acid esters.

A preferred tablet of the present invention comprises crystalline vortioxetine acetate, diluents, binders, wetting agents, disintegrants, lubricants and glidants and an enteric coating comprising film-forming polymers.

A particular preferred tablet of the present invention comprises crystalline vortioxetine acetate, mannitol, microcrystalline cellulose, sodium starch glycolate, hydroxypropylmethyl cellulose, magnesium stearate and an enteric coating comprising methacrylic acid ethyl acrylat (1:1) copolymer (commercially available as Eudragit L).

Another preferred tablet of the present invention comprises crystalline vortioxetine acetate, lactose monohydrate, silicified microcrystalline cellulose, croscarmellose sodium, polysorbate 20 (Tween 20), polyvinylpyrrolidone K30 (PVP K30), magnesium stearate and an enteric coating comprising methacrylic acid ethyl acrylat (1:1) copolymer (commercially available as Eudragit L).

A further preferred tablet of the present invention comprises crystalline vortioxetine acetate, microcrystalline cellulose, polysorbate 20 (Tween 20), polyvinylpyrrolidone K30 (PVP K30), dibasic calcium phosphate (dihydrate or anhydrate e.g. Emcompress® or anhydrous Emcompress®), magnesium stearate, starch and an enteric coating comprising methacrylic acid ethyl acrylat (1:1) copolymer (commercially available as Eudragit L).

In addition, a preferred tablet of the present invention comprises crystalline vortioxetine acetate, microcrystalline cellulose, lactose monohydrate, polysorbate 20 (Tween 20), polyvinylpyrrolidone K30 (PVP K30), magnesium stearate, starch and an enteric coating comprising methacrylic acid ethyl acrylat (1:1) copolymer (commercially available as Eudragit L).

Another preferred tablet of the present invention comprises crystalline vortioxetine acetate, microcrystalline cellulose, modified starch, polysorbate 20 (Tween 20), polyvinylpyrrolidone K30 (PVP K30), magnesium stearate and an enteric coating comprising methacrylic acid ethyl acrylat (1:1) copolymer (commercially available as Eudragit L).

In a fourth aspect, the present invention relates to the use of crystalline vortioxetine acetate for the preparation of pharmaceutical compositions. The pharmaceutical compositions are preferably solid pharmaceutical composition such as tablets and capsules or liquid pharmaceutical compositions such as syrups, elixirs, solutions and suspensions.

Form III of vortioxetine acetate is preferably used for the preparation of tablets. These tablets may be prepared by a wet granulation process comprising the steps of:
a) dry blending vortioxetine acetate form III and a part of the diluent,
b) preparing a binder solution by dissolving a binder and a wetting agent in a suitable solvent,
c) spraying the binder solution of step b) onto the mixture obtained in step a),
d) drying the obtained granulate and sieving the same,
e) mixing the obtained granulate with the remaining part of diluent and a disintegrant,
f) adding an optional glidant and/or an optional lubricant to the mixture,
g) compressing the obtained mixture into a tablet and
h) film-coating the tablet so obtained.

Suitable solvents for step b) of the herein disclosed wet granulation process include, for example, water, acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate and tetrahydrofuran.

A particular tablet of the present invention may be prepared by a wet granulation process comprising the steps of:
a) dry blending vortioxetine acetate form III and mannitol,
b) preparing a binder solution by dissolving hydroxypropylmethyl cellulose and sodium starch glycolate in a suitable solvent,
c) spraying the binder solution of step b) onto the mixture obtained in step a),
d) drying the obtained granulate and sieving the same,
e) mixing the obtained granulate with microcrystalline cellulose
f) adding magnesium stearate to the mixture,
g) compressing the obtained mixture into a tablet and
h) film-coating the tablet so obtained.

Suitable solvents in step b) of the herein disclosed wet granulation process include, for example, water, acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate and tetrahydrofuran.

Moreover, crystalline vortioxetine acetate may be used for the preparation of oral solutions. These oral solutions may be prepared by dissolving crystalline vortioxetine acetate and optionally one or more pharmaceutically acceptable excipients in a suitable solvent.

Suitable solvents which can be used for the preparation of oral solutions comprising vortioxetine acetate include water, ethanol, propylene glycol, glycerol, polyethylene glycols, poloxamers, sorbitol and benzyl alcohol.

The oral solutions prepared from crystalline vortioxetine acetate may further comprise one or more pharmaceutically acceptable excipients. Such excipients are preferably selected from the group consisting of buffers, surfactants, surface tension modifiers, viscosity modifiers, preservatives, antioxidants, coloring agents, flavouring agents, etc.

Suitable buffers which can be used for the preparation of liquid pharmaceutical compositions comprising crystalline vortioxetine acetate include weak acids such as acetic acid, phosphoric acid, succinic acid, tartaric acid, lactic acid and citric acid.

Suitable surfactants which can be used for the preparation of liquid pharmaceutical compositions comprising crystalline vortioxetine acetate include tweens, spans, monoglycerides and diglycerides.

A suitable tension modifier which can be used for the preparation of liquid pharmaceutical compositions comprising crystalline vortioxetine acetate is ethanol.

Suitable viscosity modifiers which can be used for the preparation of liquid pharmaceutical compositions comprising crystalline vortioxetine acetate include ethanol, hydroxyethylcellulose, carboxymethylcellulose sodium, methylcellulose, polyvinyl alcohol, polyvinylpyrrolidone, polyethylene glycol and glycerine.

Suitable preservatives which can be used for the preparation of liquid pharmaceutical compositions comprising crystalline vortioxetine acetate include ethanol, benzoic acid, sorbic acid, methylparaben, propylparaben and benzyl alcohol.

Suitable antioxidants which can be used for the preparation of liquid pharmaceutical compositions comprising crystalline vortioxetine acetate include propyl gallate, ascorbyl palmitate, ascorbic acid, sodium sulphite, citric acid and EDTA.

Suitable coloring agents which can be used for the preparation of liquid pharmaceutical compositions comprising crystalline vortioxetine acetate include tartrazine and sunset yellow.

In one embodiment, the present invention relates to an additional crystalline form of 1-[2-(2,4-dimethylphenylsulfanyl)phenyl]piperazine acetate, namely vortioxetine acetate form I. Form I of vortioxetine acetate is characterized by an X-ray powder diffractogram comprising characteristic peaks at 2-theta angles of 6.6±0.2°, 7.2±0.2°, 13.1±0.2°, 14.0±0.2° and 15.7±0.2°.

Form I of vortioxetine acetate is characterized by an X-ray powder diffractogram comprising characteristic peaks at 2-theta angles of 6.6±0.2°, 7.2±0.2°, 13.1±0.2°, 14.0±0.2°, 15.7±0.2°, 18.2±0.2° and 19.8±0.2° when measured using Cu-Kα radiation.

Form I of vortioxetine acetate is characterized by an X-ray powder diffractogram comprising characteristic peaks at 2-theta angles of 6.6±0.2°, 7.2±0.2°, 13.1±0.2°, 14.0±0.2°, 15.7±0.2°, 17.4±0.2°, 18.2±0.2°, 19.8±0.2°, 21.1±0.2° and 22.4±0.2° when measured using Cu-Kα radiation.

Figure 7:
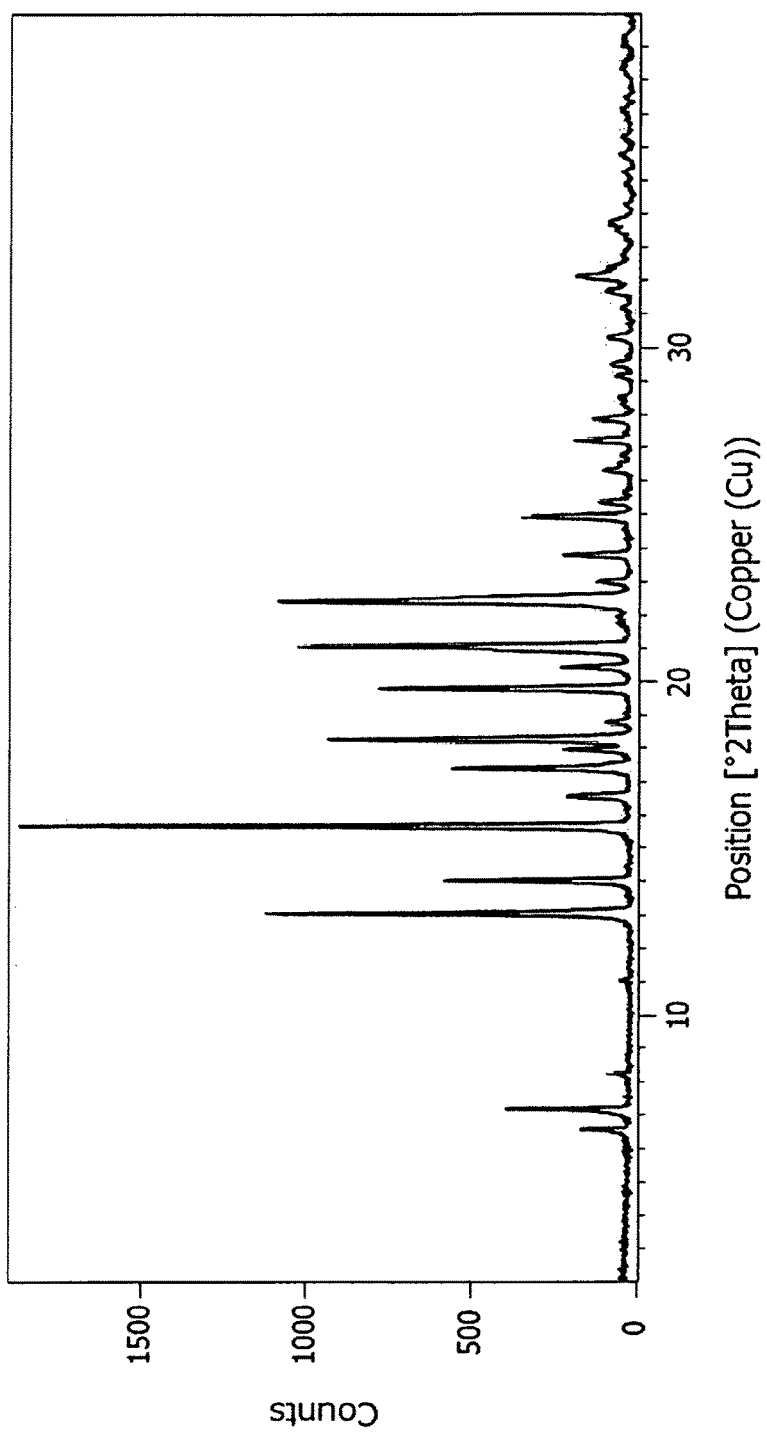
FIG. 7: X-ray powder diffractogram of vortioxetine acetate form I

The X-ray powder diffractogram of form I of vortioxetine acetate comprises additional characteristic peaks at 2-theta angles of 16.6±0.2°, 17.9±0.2°, 20.4±0.2°, 23.0±0.2°, 23.8±0.2°, 25.0±0.2°, 25.4±0.2°, 27.2±0.2°, 27.9±0.2° and 32.2±0.2°. A representative diffractogram is displayed in FIG. 7.

Examples 7 and 8 of the present invention disclose specific routes for obtaining form I of vortioxetine acetate. In brief, form I may be prepared by addition of acetic acid to vortioxetine or vice versa in a suitable solvent such as n-heptane or tert-butylmethyl ether, followed by crystallization, which is initiated by cooling, removal of the solvent or a combination thereof.

In a fifth aspect, the present invention relates to crystalline vortioxetine acetate for use as a medicament, in particular for use in the treatment of mood disorders; major depressive disorder; general anxiety disorder; post-traumatic stress disorder; depression associated with cognitive impairment, Alzheimer's disease or anxiety; depression with residual symptoms; chronic pain; or eating disorders. In one embodiment, the crystalline vortioxetine acetate used as a medicament is in form III, in another, in form I.

In one embodiment, the present invention relates to the use of crystalline vortioxetine acetate as an active pharmaceutical ingredient in a medicament, in particular as an active pharmaceutical ingredient in a medicament for the treatment of mood disorders; major depressive disorder; general anxiety disorder; post-traumatic stress disorder; depression associated with cognitive impairment, Alzheimer's disease or anxiety; depression with residual symptoms; chronic pain; or eating disorders. In one embodiment, the crystalline vortioxetine acetate used as an active pharmaceutical ingredient in a medicament is in form III, in another, in form I.

In another embodiment, the present invention relates to the use of crystalline vortioxetine acetate for the manufacture of a medicament for the treatment of mood disorders; major depressive disorder; general anxiety disorder; post-traumatic stress disorder; depression associated with cognitive impairment, Alzheimer's disease or anxiety; depression with residual symptoms; chronic pain; or eating disorders. In one embodiment, the crystalline vortioxetine acetate used for the manufacture of a medicament is in form III, in another, in form I.

In a further embodiment, the present invention relates to a method for the treatment of mood disorders; major depressive disorder; general anxiety disorder; post-traumatic stress disorder; depression associated with cognitive impairment, Alzheimer's disease or anxiety; depression with residual symptoms; chronic pain; or eating disorders, in a subject in need of such treatment, which method comprises administering to such subject a therapeutically effective amount of crystalline vortioxetine acetate. In one embodiment, the crystalline vortioxetine acetate administered to the subject is in form III, in another, in form I.

For the above-mentioned indications, the appropriate dosage will vary depending on, for example, the patient, the mode of administration, the nature and severity of the condition, disease or disorder or the effect desired. The pharmaceutical compositions for oral administration of the present invention typically comprise 5 to 50 mg, preferably 5 to 25 mg, more preferably 5 to 15 mg and most preferably 5 to 10 mg vortioxetine acetate form III or form I (calculated as vortioxetine free base).

The following specific examples, while indicating preferred embodiments of the invention, are given by way of illustration only.

EXAMPLES

Intensity data for the crystal structure were collected with Mo ($\lambda$=0.71073 Å) radiation on an Oxford Diffraction Gemini-R Ultra diffractometer at 173 K. The structure was solved using the direct methods procedure in SHELXS97 and refined by full-matrix least squares on $F^2$ using SHELXL97.

X-ray powder diffractograms (XRPD) were obtained with an X'Pert PRO diffractometer (PANalytical, Almelo, The Netherlands) equipped with a theta/theta coupled goniometer in transmission geometry, programmable XYZ stage with well plate holder, Cu-Kα1,2 radiation source (wavelength 0.15419 nm) and a solid state PIX'cel detector. The diffractograms were recorded at a tube voltage of 45 kV, tube current of 40 mA applying a step size of 0.013° 2-theta with 40 s per step (255 channels) in the angular range of 2° to 40° 2-theta at ambient conditions. A typical precision of the 2-theta values is in the range of about ±0.2° 2-theta. Thus a diffraction peak that appears at 5.0° 2-theta can appear between 4.8 and 5.2° 2-theta on most X-ray diffractometers under standard conditions.

The infrared spectrum (IR) was recorded on an MKII Golden Gate™ Single Reflection Diamond ATR (attenuated total reflection) cell with a Bruker Tensor 27 FTIR spectrometer with 4 cm$^{-1}$ resolution at ambient conditions. To record a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus an infrared peak that appears at 1716 cm$^{-1}$ can appear between 1714 and 1718 cm$^{-1}$.

Differential scanning calorimetry (DSC) was performed on a Mettler Polymer DSC R instrument. 1.7 mg sample were heated in a 40 μl aluminium pan with a pierced aluminium lid from 25 to 150° C. at a rate of 10° C./min. Nitrogen (purge rate 50 ml/min) was used as purge gas.

Thermogravimetric analysis (TGA) was performed on a Mettler TGA/DSC 1 instrument. Samples were heated in 100 μl aluminium pans closed with aluminium lids. Lids were automatically pierced at the beginning of the measurement. The sample was heated from 25 to 150° C. at a rate of 10° C./min. Nitrogen (purge rate 50 ml/min) was used as purge gas.

Moisture sorption isotherms were recorded with an SPSx-1μ moisture sorption analyzer (ProUmid, Ulm). The measurement cycle was started at 3% relative humidity (RH). Then the RH was increased from 5% to 75%, decreased to 0% and increased to 80% in 5% steps. Finally the RH was decreased to 0% in 10% steps and equilibrated in a last step to 35%. The time per step was set to a minimum of 1 hour and a maximum of 3 hours. If an equilibrium condition with a constant mass of ±0.01% within 1 hour was reached before the maximum time for all examined samples, the sequential humidity step was applied before the maximum time of 3 hours. If no equilibrium was achieved, the consecutive humidity step was applied after the maximum time of 3 hours. The temperature was 25±0.1° C. The final water content was determined by coulometric Karl Fischer titration.

Coulometric Karl Fischer titration was performed with a Metrohm 831 KF Coulometer equipped with a double-platinum detecting electrode, a Metrohm 832 KF Thermoprep oven (130° C.) and Hydranal Coulomat AK as Karl Fischer reagent.

Preparation of Vortioxetine Acetate Form III

Example 1

251 mg of vortioxetine acetate (prepared, for example, according to Example 7) was dissolved in 20 mL tert-butylmethyl ether by heating to 65° C. and the solution so obtained stirred at this temperature for an additional 30 min. Thereafter, the solution was allowed to cool to RT and the volume of the solution decreased to about ⅓ on a rotary evaporator to initiate crystallization. The crystals were collected by filtration and dried on the filter by suction.

Yield: 185 mg (74% of theory)

TABLE 3

XRPD 2-theta angles and relative peak intensities of vortioxetine acetate polymorph III prepared according to Example 1

| angle [2-theta] | relative intensity [%] | angle [2-theta] | relative intensity [%] |
|---|---|---|---|
| 8.4 | 20 | 18.5 | 51 |
| 9.7 | 50 | 18.9 | 42 |
| 10.5 | 27 | 19.6 | 36 |

TABLE 3-continued

XRPD 2-theta angles and relative peak intensities of vortioxetine acetate polymorph III prepared according to Example 1

| angle [2-theta] | relative intensity [%] | angle [2-theta] | relative intensity [%] |
|---|---|---|---|
| 11.3 | 42 | 20.2 | 14 |
| 11.8 | 34 | 21.1 | 40 |
| 12.3 | 31 | 21.4 | 15 |
| 12.5 | 40 | 21.9 | 29 |
| 13.5 | 33 | 22.3 | 61 |
| 14.8 | 11 | 22.5 | 26 |
| 15.5 | 57 | 24.7 | 20 |
| 15.6 | 58 | 25.1 | 34 |
| 16.4 | 20 | 26.2 | 10 |
| 16.6 | 55 | 26.4 | 15 |
| 16.9 | 100 | 26.6 | 20 |
| 17.2 | 10 | 26.8 | 18 |
| 17.6 | 22 | 28.3 | 11 |
| 17.9 | 54 | 30.8 | 16 |

TABLE 4

FTIR peaks of vortioxetine acetate polymorph III prepared according to Example 1
wavenumber [cm$^{-1}$]

| | | |
|---|---|---|
| 3062 | 1287 | 928 |
| 2955 | 1268 | 914 |
| 2828 | 1247 | 877 |
| 1645 | 1234 | 829 |
| 1581 | 1184 | 814 |
| 1527 | 1149 | 758 |
| 1469 | 1124 | 745 |
| 1441 | 1095 | 724 |
| 1402 | 1041 | 684 |
| 1374 | 1033 | 653 |
| 1333 | 1010 | |

Example 2

114 mg of vortioxetine acetate (prepared, for example, according to Example 7) was dissolved in 2 mL n-butyl acetate by heating to 90° C. The hot solution was filtered and allowed to cool to room temperature. The resulting crystals were collected by filtration and dried on the filter for 30 minutes by suction.

Yield: 71 mg (62% of theory)

Example 3

204 mg of vortioxetine acetate (prepared, for example, according to Example 7) was dissolved in 7 mL acetone by heating to reflux temperature. The hot solution was filtered and allowed to cool to room temperature. The resulting crystals were collected by filtration and dried on the filter for 15 min by suction.

Yield: 79 mg (39% of theory)

Example 4

175 mg vortioxetine acetate (prepared, for example, according to Example 7) was dissolved in 1.5 mL isobutyl acetate by heating to 85° C. The clear solution was allowed to cool to room temperature. The resulting crystals were collected by filtration, dried for 30 min on the filter by suction and further dried at 40° C. under vacuum (<40 mbar) for 4 hours.

Yield: 108 mg (62% of theory).

Example 5

170 mg of vortioxetine acetate (prepared, for example, according to Example 7) was dissolved in 2 mL toluene by heating to 100° C. The hot solution was filtered and allowed to cool to room temperature. The resulting crystals were collected by filtration and dried at 40° C. under vacuum (<40 mbar) for 1 hour.

Yield: 90 mg (53% of theory)

Example 6

3.70 g vortioxetine acetate (prepared, for example, according to Example 7) was dissolved in 400 mL diisopropyl by heating to 85° C. The hot solution was filtered, cooled in an ice-bath and stored in a refrigerator (5±2° C.) for 15 h. The obtained crystals were collected by filtration and dried on the filter by suction.

Yield: 2.93 g (79% of theory)

The crystals obtained in each of Examples 2 to 6 were analysed by XRPD and found to be the same polymorph of vortioxetine acetate as obtained in Example 1, namely form III.

Preparation of Vortioxetine Acetate Form I

Example 7

7.3 g of vortioxetine hydrobromide was dissolved in 140 mL ethyl acetate and 140 mL 5M NaOH solution for 30 min at 70° C. The biphasic reaction mixture was cooled to RT and filtered through a folded filter into a separation funnel. The aqueous phase was extracted with 100 mL ethyl acetate twice, the combined organic phases were washed with 250 mL water twice and dried with $Na_2SO_4$. The solvent was evaporated on a rotavapor at 40° C. subsequently. The crystalline crude product was recrystallized by dissolving it in 50 mL acetonitrile at 85° C. and allowing the clear solution to cool to RT. The crystallization product was collected by filtration and dried under suction. Vortioxetine free base was confirmed by XRPD Yield: 3.78 g (66% of theory).

200 mg vortioxetine free base was dissolved in 10 mL n-heptane at 50° C. 38 μL (1.0 mol equivalent) glacial acetic acid was added, whereupon precipitation was observed. The mixture was allowed to cool to room temperature before the crystals were isolated by filtration and dried under vacuum (<40 mbar).

Yield: 212 mg (88% of theory).

TABLE 5

XRPD 2-theta angles and relative peak intensities of vortioxetine acetate Form I prepared according to Example 7

| angle [2-theta] | relative intensity [%] |
|---|---|
| 6.6 | 8 |
| 7.2 | 20 |
| 13.1 | 60 |
| 14.0 | 31 |
| 15.7 | 100 |
| 16.6 | 9 |
| 17.4 | 28 |
| 17.9 | 10 |
| 18.2 | 49 |
| 19.8 | 41 |
| 20.4 | 11 |
| 21.1 | 53 |
| 22.4 | 54 |
| 23.0 | 5 |
| 23.8 | 11 |
| 25.0 | 17 |
| 25.4 | 5 |
| 27.2 | 8 |
| 27.9 | 6 |
| 32.2 | 9 |

Example 8

200 mg vortioxetine free base was dissolved in 7 mL tert-butylmethyl ether at 50° C. 38 μL (1.0 mol equivalent) glacial acetic acid was added and the solution stirred for 10 min at 50° C. Thereafter, the solution was allowed to cool to room temperature, whereupon crystallization was observed. The obtained suspension was kept at room temperature for an additional hour before the crystals were collected by filtration and dried under vacuum (<40 mbar).

Yield: 126 mg (52% of theory)

The crystals obtained in Examples 8 were analysed by XRPD and found to be the same polymorph of vortioxetine acetate as obtained in Example 7, namely form I.

Water Solubility Determination of Vortioxetine Acetate Form III

Example 9

100 μL water was added to 100.34 mg of vortioxetine acetate form Ill. The mixture was vigorously shaken for 2 min and placed at 25° C. for 15 min. The solid was not completely dissolved, therefore a further 100 μL of water was added and the dissolving procedure repeated. Dissolution occurred after the addition of 300 μL water in total, corresponding to a solubility of 334 mg/mL of the acetate salt. According to Equation 1 this corresponds to a solubility of 278 mg free base/mL.

$$\text{solubility(free base)} = \frac{\text{solubility(acetate salt)} * \text{MW(base)}}{\text{MW(acetate salt)}} \qquad \text{Equation 1}$$

MW(free base) = 298.45 g/mol

MW(acetate salt) = 358.50 g/mol

Stress Tests with Vortioxetine Acetate Form III

Example 10

42 mg of vortioxetine acetate form Ill was stressed at 40° C./75% RH for 4 weeks. Subsequent XRPD analysis confirmed that polymorph Ill underwent no structural changes.

Example 11

34 mg of vortioxetine acetate form Ill were stressed at RT/97% RH for 4 weeks. Subsequent XRPD analysis confirmed that polymorph Ill underwent no structural changes.

Determination of the Thermodynamically Stability of Vortioxetine Acetate

Example 12

35 mg of vortioxetine acetate form III was suspended in 0.5 mL n-heptane and stirred with a magnetic stirrer at room temperature for 4 weeks. Subsequent XRPD analysis confirmed that polymorph III underwent no structural changes.

Example 13

25 mg of vortioxetine acetate form I was suspended in 0.5 mL n-heptane and stirred with a magnetic stirrer at room temperature for 24 h. Subsequent XRPD analysis confirmed that polymorph I transformed to form III indicating that form III is the more thermodynamically stable form at room temperature.

The invention claimed is:

1. Vortioxetine acetate in crystalline form having an X-ray powder diffractogram comprising peaks at 2-theta angles of 9.7±0.2°, 11.3±0.2°, 13.5±0.2°, 15.6±0.2° and 16.9±0.2° when measured using Cu-Kα radiation.

2. A crystalline form of vortioxetine acetate according to claim 1 exhibiting monoclinic unit cells having space group C2/c and having the parameters
   a=34.18+/−0.5 Angstrom
   b=10.72+/−0.2 Angstrom
   c=21.01+/−0.3 Angstrom
   α=90.0°
   β=97.9°+/−0.5°
   γ=90°
   Z=16
as determined by X-ray structural analysis.

3. A crystalline form of vortioxetine acetate according to claim 1 characterized by an infrared spectrum comprising peaks at wave numbers of 2828±2 $cm^{-1}$, 1645±2 $cm^{-1}$, 1527±2 $cm^{-1}$, 1402±2 $cm^{-1}$ and 653±2 $cm^{-1}$.

4. A crystalline form of vortioxetine acetate according to claim 1 having a water content of less than 0.7% at a relative humidity of ≤80%.

5. A crystalline form of vortioxetine acetate characterized by an X-ray powder diffractogram comprising characteristic peaks at 2-theta angles of 6.6±0.2°, 7.2±0.2°, 13.1±0.2°, 14.0±0.2° and 15.7±0.2° when measured using Cu-Kα radiation.

6. A process for the preparation of crystalline vortioxetine acetate according to claim 1 comprising the steps of (a) dissolving vortioxetine acetate in a solvent upon heating,
(b) optionally filtering the solution and
(c) cooling the solution in order to initiate crystallization.

7. A process according to claim 6, wherein the solvent is selected from tert-butylmethyl ether; diisopropyl ether, n-heptane, n-butyl acetate, isobutyl acetate, toluene or acetone.

8. A solid pharmaceutical composition comprising a crystalline form of vortioxetine acetate according to claim 1 and further comprising at least one pharmaceutically acceptable excipient.

9. A solid pharmaceutical composition according to claim 8, which is a tablet or capsule.

10. A solid pharmaceutical composition according to claim 9 which is an enteric coated tablet or capsule.

11. An oral solution comprising vortioxetine acetate and optionally one or more pharmaceutically acceptable excipients, the vortioxetine acetate having an X-ray powder diffractogram comprising peaks 2-theta angles of 9.7±0.2°, 11.3±0.2°, 13.5±0.2°, 15.6±0.2° and 16.9±0.2° when measured using Cu-Kα radiation or an X-ray powder diffractogram comprising peaks at 2-theta angles of 6.6±0.2°, 7.2±0.2°, 13.1±0.2°, 14.0±0.2° and 15.7±0.2° when measured using Cu-Kα radiation.

12. A method for the production of a pharmaceutical composition for oral administration, comprising
   providing a crystalline form of vortioxetine acetate according to claim 1;
   providing at least one pharmaceutically acceptable excipient; and
   combining the crystalline form of vortioxetine acetate with the at least one pharmaceutically acceptable excipient to form a pharmaceutical composition for oral administration.

13. A crystalline form of vortioxetine acetate according to claim 1, wherein the crystalline form of vortioxetine acetate is provided as a medicament.

14. A method for treating mood disorders; major depressive disorder; general anxiety disorder; post-traumatic stress disorder; depression associated with cognitive impairment, Alzheimer's disease or anxiety; depression with residual symptoms; chronic pain; or eating disorders in a subject in need thereof, comprising
   administering a crystalline form of vortioxetine acetate according to claim 1.

* * * * *